(12) United States Patent
Ancar

(10) Patent No.: US 10,363,006 B2
(45) Date of Patent: *Jul. 30, 2019

(54) MOBILE IMAGING SYSTEM AND METHOD

(71) Applicant: Terry L. Ancar, Kenner, LA (US)

(72) Inventor: Terry L. Ancar, Kenner, LA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/888,439

(22) Filed: Feb. 5, 2018

(65) Prior Publication Data

US 2018/0153488 A1 Jun. 7, 2018

Related U.S. Application Data

(63) Continuation of application No. 15/616,121, filed on Jun. 7, 2017, now Pat. No. 9,918,684, which is a (Continued)

(51) Int. Cl.
*A61B 6/00* (2006.01)
*A61B 6/08* (2006.01)
*G03B 42/02* (2006.01)

(52) U.S. Cl.
CPC .............. *A61B 6/4405* (2013.01); *A61B 6/08* (2013.01); *A61B 6/4233* (2013.01); *A61B 6/461* (2013.01); *A61B 6/465* (2013.01); *A61B 6/467* (2013.01); *A61B 6/487* (2013.01); *A61B 6/547* (2013.01); *A61B 6/587* (2013.01); *A61B 6/588* (2013.01); *G03B 42/02* (2013.01); *A61B 6/4494* (2013.01)

(58) Field of Classification Search
CPC ...... A61B 6/4035; A61B 6/4291; A61B 6/484; A61B 6/4458; A61B 6/4405; A61B 6/547; A61B 6/587; G01N 23/20008; G01N 23/20075
See application file for complete search history.

(56) References Cited

U.S. PATENT DOCUMENTS 6,859,521 B2 2/2005 Spahn
7,142,638 B2 11/2006 Polichar et al.
(Continued)

FOREIGN PATENT DOCUMENTS

DE 10 2010 008 552 A1 8/2011
WO 2004/010381 A1 1/2004
WO 2006/008677 A1 1/2006

*Primary Examiner* — Dani Fox
(74) *Attorney, Agent, or Firm* — Marin Patents LP; Gustavo Marin

(57) ABSTRACT

A mobile fluoroscopic imaging system having a portable radiation source capable of emitting radiation in both single and, alternatively, pulse emissions and adapted to move in all degrees of freedom; a portable detector operable to detect radiation from the radiation source, wherein the detector is adapted to move independently of the radiation source in all degrees of freedom; the radiation source and detector each comprises an alignment sensor in communication with a computer; the computer is in communication with the radiation source and the detector; the position, distance and orientation of the radiation source and the detector are established by the computer; and the computer sends an activation signal to the radiation source to indicate when radiation may be emitted. Preferably, the radiation source is prevented from emission of radiation until the detector and the radiation source have achieved predetermined alignment conditions.

12 Claims, 9 Drawing Sheets

Related U.S. Application Data continuation of application No. 14/396,003, filed on Oct. 21, 2014, now Pat. No. 9,693,746.

(60) Provisional application No. 61/637,733, filed on Apr. 24, 2012.

(56) References Cited

U.S. PATENT DOCUMENTS

2010/0123083 A1  5/2010  Petrick et al.
2012/0087474 A1  4/2012  Foos

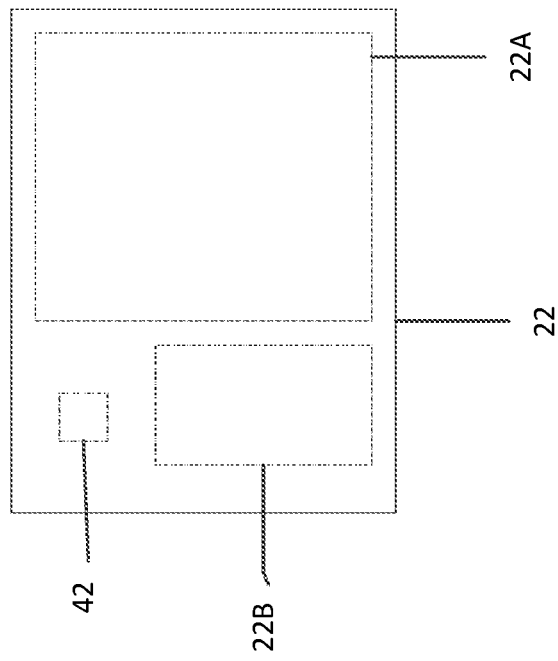
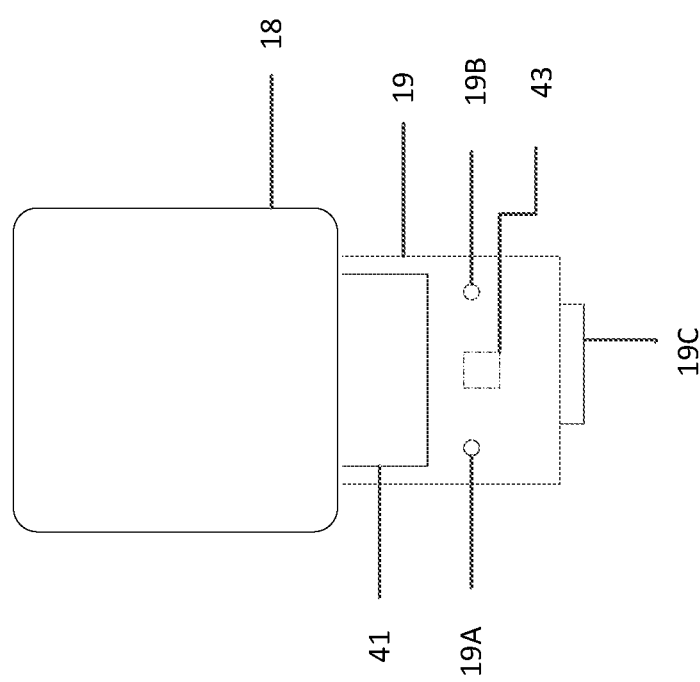

MOBILE IMAGING SYSTEM AND METHOD

CROSS-REFERENCE TO RELATED APPLICATIONS

This Application is a continuation to U.S. patent application Ser. No. 15/616,121 titled, "MOBILE IMAGING SYSTEM AND METHOD" filed on Jun. 7, 2017 which is a continuation U.S. patent application Ser. No. 14/396,003 titled "MOBILE IMAGING SYSTEM AND METHOD," filed on Oct. 21, 2014, which of claims the benefit of the priority of U.S. Provisional Patent Appl. No. 61/637,733, filed on Apr. 24, 2012, the disclosures of which are incorporated herein by reference.

BACKGROUND OF THE INVENTION

Field of the Art

The present invention relates to devices and methods used to obtain radiography images, and to such devices in which a detector and a radiation source are in communication with a computer regarding orientation and location of the detector and the radiation source.

Discussion of the State of the Art

Modern medical facilities such as hospital or emergency care facilities are often large and complex organizations. A medical facility may be organized into various departments or branches that specialize in a particular type of patient care or expertise. For example, a medical facility may have a radiology department that handles various medical imaging tasks such as computed tomography (CT) systems, X-ray system (including both conventional and digital or digitized imaging systems), magnetic resonance imaging (MRI) systems, position emission tomography (PET) system, ultrasound systems, nuclear medicine systems, and the like. Such systems provide invaluable tools for identifying, diagnosing and treating physical conditions and greatly reduce the need for surgical diagnostic intervention. In many instances, these modalities complement one another and offer the physician a range of techniques for imaging particular types of tissue, organs, physiological systems, and so forth However, patients requiring an X-ray, for example, must often be transported to the radiology department or even a separate and geographically distant imaging center. This can present additional delays, costs, and in conveniences to the patient and practitioners.

Digital imaging systems are becoming increasingly widespread for producing digital data that can be reconstructed into useful radiographic images. In one application of a digital imaging system, radiation from a source is directed toward a subject, typically a patient in a medical diagnostic application, and a portion of the radiation Passes through the subject and impacts a detector. The surface of the detector converts the radiation to light photons, which are sensed. The detector is divided into an array of discrete picture elements or pixels, and encodes output signals based upon the quantity or intensity of the radiation impacting each pixel region. Because the radiation intensity is altered as the radiation passes through the subject, the images reconstructed based upon the output signals may provide a projection of tissues and other features similar to those available through conventional photographic film techniques.

In use, the signals generated at the pixel locations of the detector are sampled and digitized. The digital values are transmitted to Processing circuitry where they are filtered, scaled, and further processed to produce the image data set. The data set may then be used to reconstruct the resulting image, and display the image.

A number or devices have been conceived to address the needs or portable radiography including developments in portable units, detectors, and related digital imaging features. For example, U.S. Pat. No. 7,016,467 issued to Brooks discloses a mobile x-ray apparatus for generating a digital x-ray image and transmitting it to a remote site. The device includes a first computer, a flat panel detector in communication with the first computer, and an x-ray cart assembly irremovably supporting the first computer, which includes a cart with a battery charger and an x-ray machine in communication with the flat panel detector. It further includes an x-ray tube extendible from the cart, and a mechanism for framing a target body area of a patient.

U.S. Pat. No. 7,342,998 issued to Kump, et al., discloses an x-ray system quick-connect connection to allow an end-user to de-couple a portable x-ray detector from an x-ray scanner/host.

U.S. Pat. No. 7,43428,470 issued to Koren discloses a mobile computed radiography unit. This system includes a scanner adapted to acquire one or more images from an image recording medium, a frame that supports the scanner, an x-ray source mounted to the frame, a transport mechanism coupled to the frame and adapted to facilitate transport of the mobile apparatus between locations, and a display coupled to the frame and connected to the scanner to display the images acquired by the scanner.

U.S. Pat. No. 7,783,008 issued to Jabri describes a technique for placing markers on digital radiographic images, such as projection x-ray and tomosynthesis images. A tag encoding data is disposed on or near a component of a radiographic imaging system, such as on a digital detector. The tag is read during an imaging session, and human readable indicia for the marker is generated that can be permanently included in the resulting images or displayed when desired, such as in an overlay.

U.S. Pat. No. 7,798,710 issued to Barnes discloses a mobile radiographic unit with improved x-ray scatter control. Improved x-ray scatter control is provided through the alignment of the system with the focal line of an anti-scatter grid. In a preferred embodiment, the system comprises an x-ray source assembly, a tube housing mounting, a measuring system, a motion control system and a processor in communication with the measuring system and the motion control system. The system attempts to establish an optimal alignment, although it discloses no means for controlling or preventing the emission of radiation.

U.S. Pat. No. 7,817,040 issued to Homanfar, et al., discloses a radio frequency identification (RFID) system which detects conditions of alignment, wherein the system may be used with hand-held, fixed-in-place, stationary, and permanently mounted apparatus. An RF interrogator, an RF transponder, and an x-ray sensitive imaging device, and its holder are configured to be critically aligned to a dental x-ray machine head apparatus, rendering repeat imaging unnecessary. The x-ray emitter may be further configured to automatically obtain a desired x-ray image or configured so that the device cannot activate and provide a radiograph until alignment with the transponder and associated x-ray sensitive imaging device has occurred. A key limitation of this system is its reliance on RFID methods to determine orientation and location, because radio frequencies may interfere with other critical or life support equipment such as in an intensive care unit (ICU). There is also no mention of other methods to determine orientation and location, such as inertial measurement units (IMU's), or other features which would make this device suitable for use in the context of an ICU or neonatal ICU (NICU).

U.S. Pat. No. 7,947,960 issued to Wu, et al., discloses a portable detector panel including an x-ray detector assembly having an x-ray detecting surface on its surface, a box-like case that houses the x-ray detector assembly therein and whose upper part that is opposite to the x-ray detecting surface is x-ray transmissive.

U.S. Pat. No. 8,04141,045 issued to Foos, et al., discloses a mobile digital radiography system including a mobile x-ray source; a mobile computer, the computer having a display for radiographic images and related information; and a digital radiography detector, the detector and x-ray source in communication with and under control of the computer. No alignment features are disclosed in this system, nor any functionality to control or prevent the emission of radiation based on alignment or location of the detector.

U.S. Publication No. 2002/015041415 invented by Barnes, et al., discloses a mobile radiographic unit with improved x-ray scatter control. Improved x-ray scatter control is provided through the alignment of the system with the focal line of an anti-scatter grid. The system comprises an x-ray source assembly, a tube housing mounting, an automatic measuring means, a motion control means and a processing means in communication with the automatic measuring system and the motion control system. Although, the alignment of the system occurs with minimal input by the operator, there is no means provided which controls or prevents the emission of the radiation source based on the alignment condition.

U.S. Publication No. 2008/014242837 invented by Heath, et al., discloses a position sensing apparatus for radiation imaging. The system includes a radiation head with a radiation source and an adjustable angular orientation. A radiation image detection device has a photostimulable medium (such as a detector) that records an image according to radiation emitted from the radiation source. A measurement sensor apparatus, preferably inertial, is coupled to the detector to provide three-dimensional data for determining the orientation of the photostimulable medium. There is at least one indicator responsive to the orientation data from the measurement sensor apparatus for indicating an orientation adjustment of the radiation source is needed in at least one direction. While this system attempts to establish orientation of the detector and radiation source, the system does not control or prevent the emission of radiation from the radiation source.

Despite the foregoing advances in the art, there remain significant shortcomings in existing systems used for diagnostic imaging. Current mobile radiography/fluoroscopic imaging systems are cumbersome and expensive. These mobile systems normally incorporate a fixed, mechanical C-Arm, or other mechanical configuration which connects the radiation source and the detector to one another, in order to mechanically fix the detector relative to the x-ray source to prevent misalignment outside of normally government-regulated, pre-determined tolerances. In addition, the spatial location of the detector is not always known relative to the x-ray source, as is the case in fixed, permanent digital radiography/fluoroscopic (DR) imaging systems. Especially when the subject to be imaged is very fragile or largely immobile, the need continues to exist for mobile systems which comply with applicable governmental regulations, while being easy and safe to use in a variety of settings.

SUMMARY OF THE INVENTION

The present invention is deemed to meet this need, amongst others, in a highly facile and effective way. In particular, the present invention provides a mobile system which enables users to substantially continuously know the spatial location of the detector relative to the x-ray source. The x-ray source can more easily be aligned, and monitored for maintenance of alignment, with the portable detector within predetermined tolerances during procedures. In preferred embodiments, the invention further provides radiation interlock switch to prevent the emission of radiation if, for whatever reason, the x-ray source and detector are not aligned within the predetermine tolerance (s).

Thus, in one embodiment of this invention a mobile radiography/fluoroscopic imaging system is provided, comprising a portable radiation source operable to emit radiation in a single exposure (radiographic) or pulse (fluoroscopic) exposures, wherein the X-Ray source is adapted to move in all degrees of freedom; a portable detector operable to detect the radiation in single (radiographic) or pulse (fluoroscopic) emission from the radiation source, wherein the detector is adapted to move independently of the radiation source in all degrees of freedom; and wherein the radiation source and the detector each includes an alignment sensor in communication with a computer; wherein the computer is in communication with the radiation source and the detector; and wherein the position and/or orientation of the radiation source and the detector are established by the computer, and wherein the computer sends an activation signal to the radiation source to indicate when radiation may be emitted.

In a preferred embodiment, the radiation source and the detector each includes an motion tracking device (MTD) to detect position and/or orientation relative to one another. For purposes of the present disclosure, position refers to x and y axes location of an object, distance refers to the z axis delta between two objects' locations, and orientation refers to the roll, pitch and yaw of an object.

Advantageously, the detector may be visually obscured from the radiation source.

In a further preferred embodiment, the radiation source is prevented from emission of radiation until the detector and the radiation source have achieved predetermined alignment conditions.

In another embodiment, emission of radiation from the radiation source is automatically performed upon and during achievement of predetermined alignment conditions between the detector and the radiation source.

Preferably, the radiation source is capable of emitting radiation in a single emission and in pulsed emissions.

The invention may further include an indicator adapted to notify an operator when the detector and the radiation source have achieved predetermined alignment conditions, wherein the indicator is a visible indicator or an audible indicator.

In a further embodiment, the indicator is adapted to notify an operator when the detector is within a predetermined range of the radiation source.

In a more preferred embodiment, the detector is a portable, flat panel, digital X-ray detector.

Preferably, the computer includes software adapted to receive position and/or orientation signals from the alignment sensors, and further adapted to send alignment data from the alignment sensors to the radiation source.

Yet another embodiment of the invention provides an improvement to a medical procedure which sends radiation through a subject in order to produce radiological images of the subject, the improvement comprising:

placing the subject between a portable detector and a portable radiation source, the portable detector being operable to detect radiation from the portable radiation source, wherein the detector and the radiation source are each adapted to move independent of one another and to move in all degrees of freedom, and the radiation source and the detector each comprises an alignment sensor in communication with a computer;

placing the computer in communication with the radiation source and the detector; and operating the computer so as to establish the position, distance and/or orientation of the radiation source and the detector, and so as to send an activation signal to the radiation source to indicate when radiation may be emitted. Preferably, the radiation source is also adapted to emit radiation in both single and, alternatively, pulse emissions (e.g., for use in fluoroscopic procedures).

In another embodiment, the aforesaid improvement further comprises automatically preventing the radiation source from emitting radiation until the detector and the radiation source have achieved one or more predetermined alignment conditions.

Yet another embodiment of the aforesaid improvement further comprising automatically triggering the emission of radiation from the radiation source upon and during achievement of one or more predetermined alignment conditions between the detector and the radiation source.

These and still other embodiments, features and advantages of the invention will now become even more apparent from the accompanying figures, detailed description and claims.

BRIEF DESCRIPTION OF THE DRAWING FIGURES

For a further understanding of the nature, embodiments and advantages of the present invention, reference should be had to the following detailed description, read in conjunction with the following drawings, wherein like reference letters or numerals denote like elements.

FIG. 5a illustrates an enlarged, side, partially phantom view of the portable radiation source of the device if FIG. 1.

FIG. 5b illustrates an enlarged, top, partially phantom view of the portable x-ray detector used in conjunction with the device of FIG. 1.

DETAILED DESCRIPTION

To fully understand the invention in its various embodiments and the improvements the invention provides, first we have to review a number of key challenges a mobile radiographic/fluoroscopic system must address.

Figure 1:
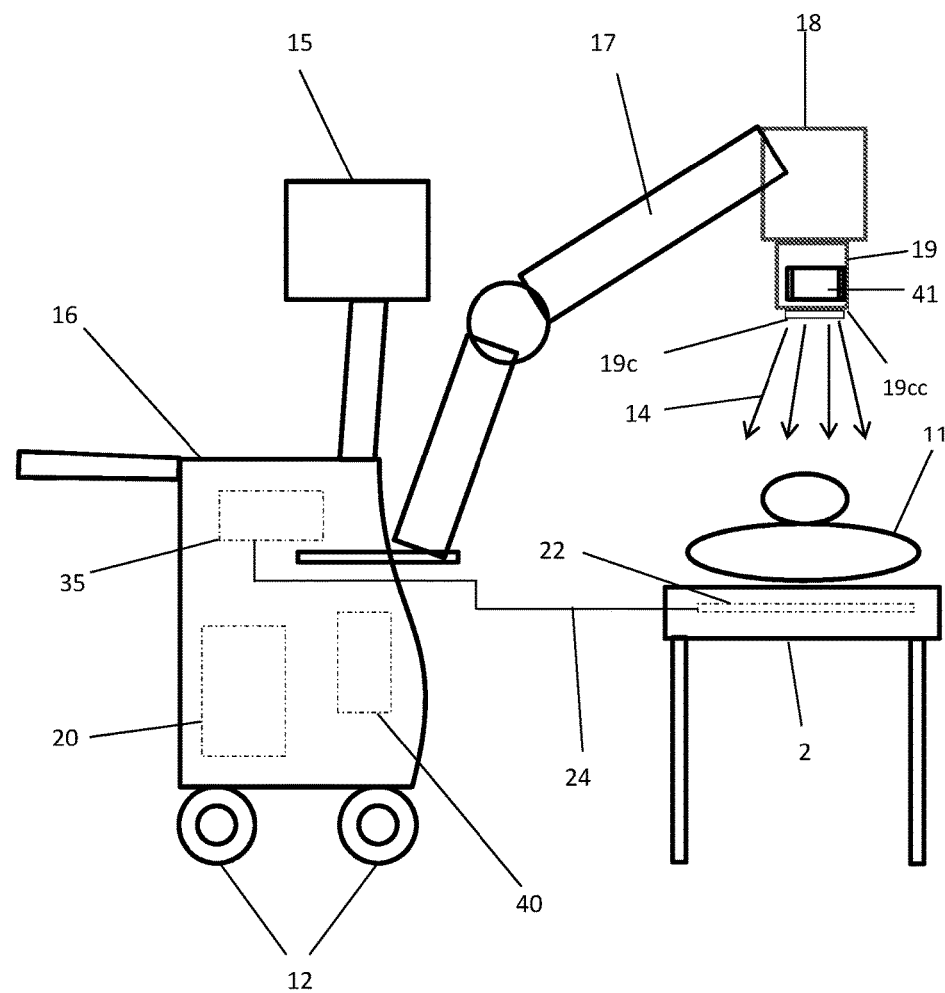
FIG. 1 illustrates a side view of a mobile imaging system applying radiation to a subject in accordance with a preferred embodiment of the invention

A mobile radiography imaging system, comprising a portable radiation source (such as, e.g., an X-ray source 18 as seen in FIG. 1) adapted to move in all degrees of freedom; a portable detector (such as a portable detector 22 as seen in FIG. 1) operable to detect the radiation from the radiation source, wherein the detector is adapted to move independently of the radiation source in all degrees of freedom. The patient may not necessarily be in a horizontal position for the X-Ray exanimation, but may be at an angle, depending on the type of exanimation required and the ability to move the patient for the exanimation. More importantly, if an X-Ray radiograph is captured and the portable detector and X-Ray source are not aligned within one or more predetermined tolerances, the quality and amount of radiation could be comprised, usually causing a retake of the X-Ray radiograph, requiring the patient to receive additional radiation dose. To perform fluoroscopic procedures, certain governmental agencies, e.g., the US FDA, may require that the x-ray source and portable detector must be aligned within one or more predetermined tolerances. Thus, if the x-ray source and portable detector are not aligned within the predetermine tolerance(s), in accordance with this invention a radiation source exposure interlock 18A (as seen, e.g., on FIG. 6) should be activated preventing the x-ray source from emitting radiation into the subject or patient.

Before the subject invention is further described, it is to be understood that invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Although a radiographic system is described in this description, the concepts are equally applicable to a radiographic/fluoroscopic system as well. In fact, these system of this invention is in many respects particularly and preferably adapted for use in fluoroscopic procedures, because of the need for safe control of x-ray emissions from a pulsed radiation source employed during fluoroscopic procedures. The safety features of this system facilitate the judicious use of and exposure to x-ray radiation during fluoroscopic procedures carried out using a mobile system, and is particular beneficial when applied to subjects who are immobile or fragile and cannot be ported easily for radiological procedures.

Referring generally to FIG. 1, a mobile X-ray imaging system is presented, referenced generally by reference numeral 16. In the illustrated embodiment, the mobile X-ray imaging system 16 is a digital X-ray system that is designed both to acquire radiographic and/or fluoroscopic image data and to process the image data for display in accordance with the present techniques. In particular, the system 16 is operable to produce both radiographic images and fluoroscopic images.

Figure 9:
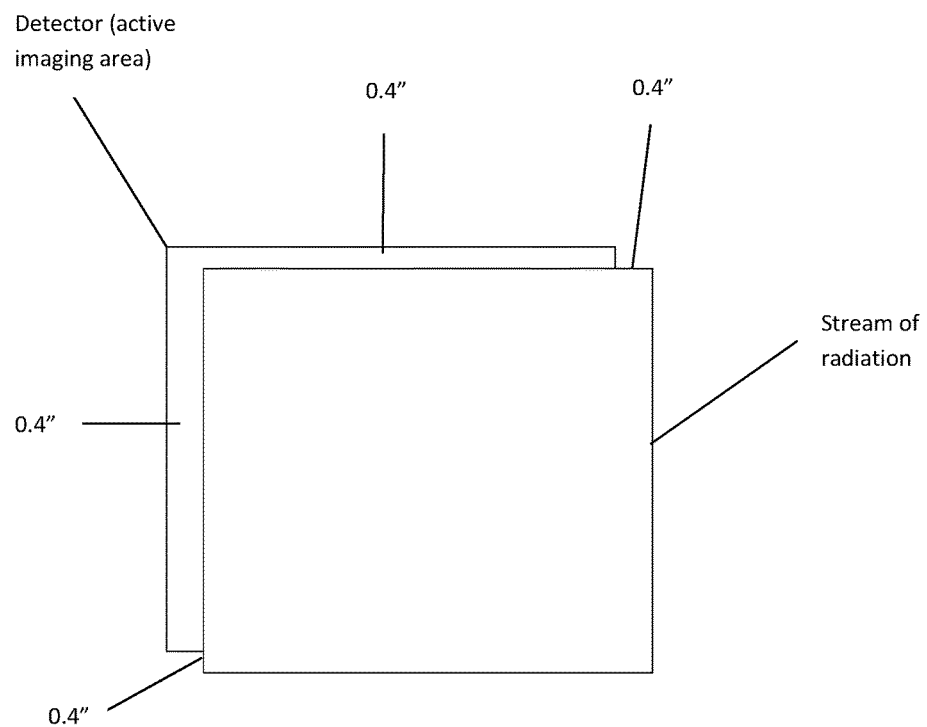
FIG. 9 is a schematic representation of alignment dimensions and tolerances for a radiation detector and a stream of radiation emitted by a radiation source.

In the preferred embodiment of FIG. 1, the mobile radiology imaging system 16 generally comprises a portable cart having caster wheels 12, a radiation (X-ray) source 18 operatively attached to a manipulatable arm 17 and capable of moving in all degrees of freedom, and a portable flat-panel digital radiation (X-ray) detector 22. Importantly, the x-ray source 18 and the detector 22 are capable of producing both radiographic (via single radiation emissions) and fluoroscopic X-ray images (via pulse radiation emissions). The imaging system 16 also includes a collimator 19 attach to the radiation source 18, which permits a controlled stream of radiation 14 to pass into a region in which a patient 11 is positioned on a table 2. For fluoroscopic procedures a Lead aperture 19*c* and lead aperture interlock 19*cc* ensures that the stream of radiation 14 does not exceed the size of the active image area 22*a* of the detector 22 further described. The controlled stream of radiation 14 passes through the patient 11 and impacts the detector 22. The detector 22 converts the X-ray photons received on its surface to lower energy photons, and subsequently to electric signals, which are acquired and processed to reconstruct an image of the features within the patient 11. As can be appreciated from FIG. 1, alignment between the radiation source 18 and the detector 22 and size of stream of radiation 14 is of critical importance. If the radiation source 18 and the detector 22 are not aligned, a portion of the stream of radiation 14 may not pass through the patient 11 at the intended position, orientation or angle, so the stream of radiation 14 cannot be properly received by the detector 22, and an accurate image of the patient 11 cannot be obtained. Furthermore, even if the detector 22 is directly in line with the radiation source 18, the detector 22 must be oriented such that its plane is perpendicular to the radiation source 18 for proper detection of the radiation 14. In addition for fluoroscopic procedures, alignment and stream of radiation 14 must conform to regulatory standards for alignment of the radiation stream size of x-ray source 18 to detector 22, if x-ray source 18 is not within alignment tolerance, or stream of radiation 14 is not the proper size, the alignment system must inhibit x-ray source 18 from producing radiation 14. The tolerances may vary, but will typically be 2% of the distance between the radiation source and detector (SID; source image distance). The predetermined alignment conditions of this invention also may vary, but typically in the United States, for example, will be one or more of SID is usually set at 40 inches, (40 inches×0.2=0.8 inches total) radiation source and detector cannot be more than 0.4 inch off the center axis. In this regard, see FIG. 9 further illustrating such tolerances in a schematic of the detector area and the radiation stream area.

In an operating configuration, a patient 11 is positioned on a table or other patient support 2 and located between the radiation source 18 and the detector 22. The detector 22 can be coupled via data cable 24 to a workstation computer 35 which commands acquisition of the signals generated in the detector 22, although wireless communication between the detector 22 and the computer is the more preferred method. As the detector receives radiation 14 that pass through the patient 11, imaging data is transmitted to the workstation computer 35. In most cases, the workstation computer 35 may also execute various signal processing and filtration functions, such as for initial adjustment of dynamic ranges, interleaving of digital image data, and so forth. The workstation 35 also enables a user to control the operation of the system to produce a desired image. Images processed by the workstation 35 are displayed on a monitor 15. Electrical power for the radiation source 18, workstation computer 35, and the digital detector 22 is provided by a conventional power supply 20 located within the cart, and which may be provide by batteries or electrically connected to any available 110 VAC power source.

Figure 2:
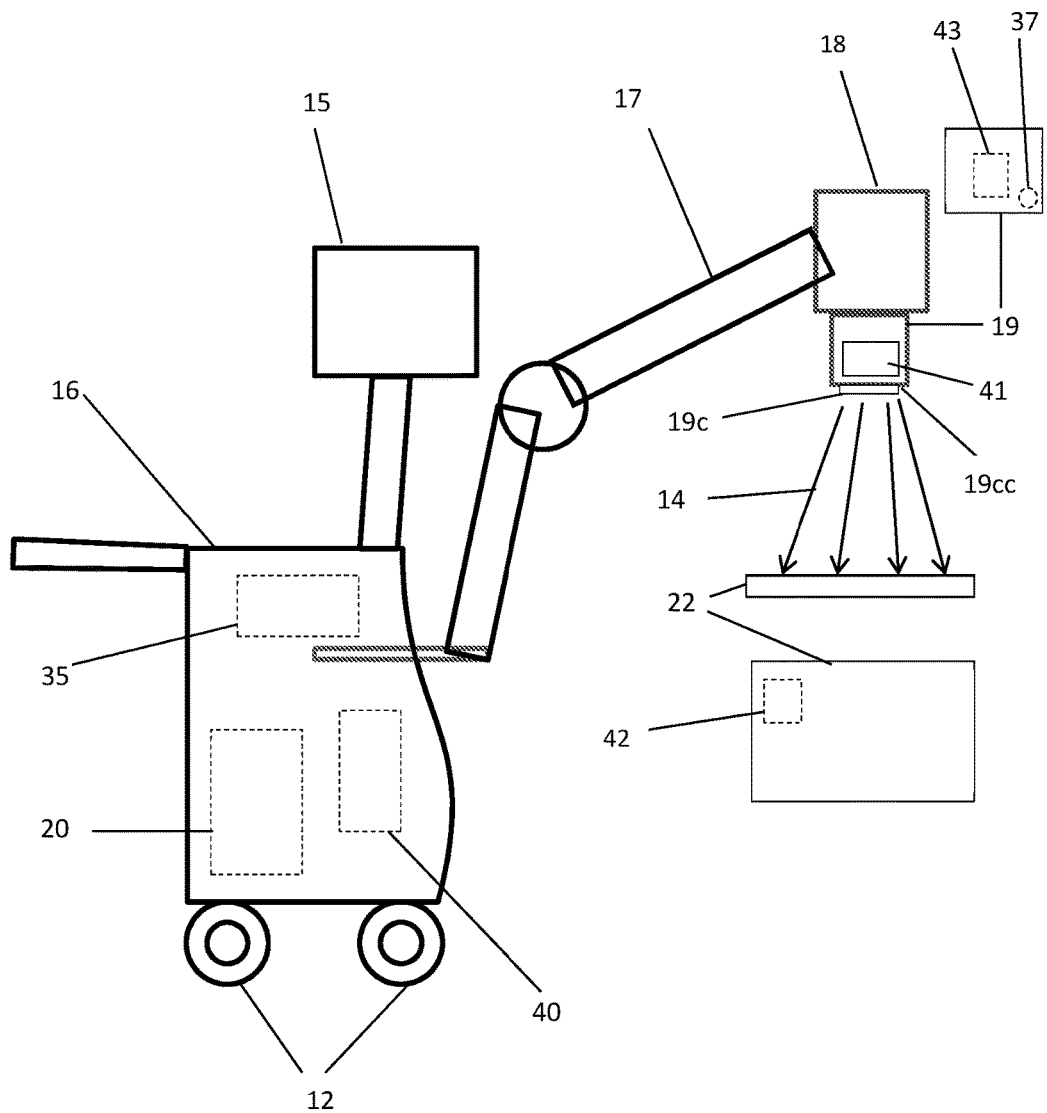
FIG. 2 illustrates a more detailed side view of the device of FIG. 1 (with the subject present) depicting the position and orientation sensors.

Because movement of the detector 22 is independent of the radiation source 18, it is possible for the stream of radiation 14 to strike the detector 22 at an angle or not centered to the detector 22, producing inaccurate images of the patient 11. As shown more clearly in FIG. 2, the radiation source 18 and the detector 22 each have an alignment sensor/transmitter 43, 42 in the form of, for example, an motion tracking device (MTD), which establishes both the location and orientation of the respective radiation source 18 and detector 22 relative to one another. The sensor/transmitters 42, 43 are used to align the detector 22 with the radiation source 18 to ensure that the radiation 14 from the radiation source 18 strikes the detector 22 at the correct angle, position and orientation.

Figure 6:
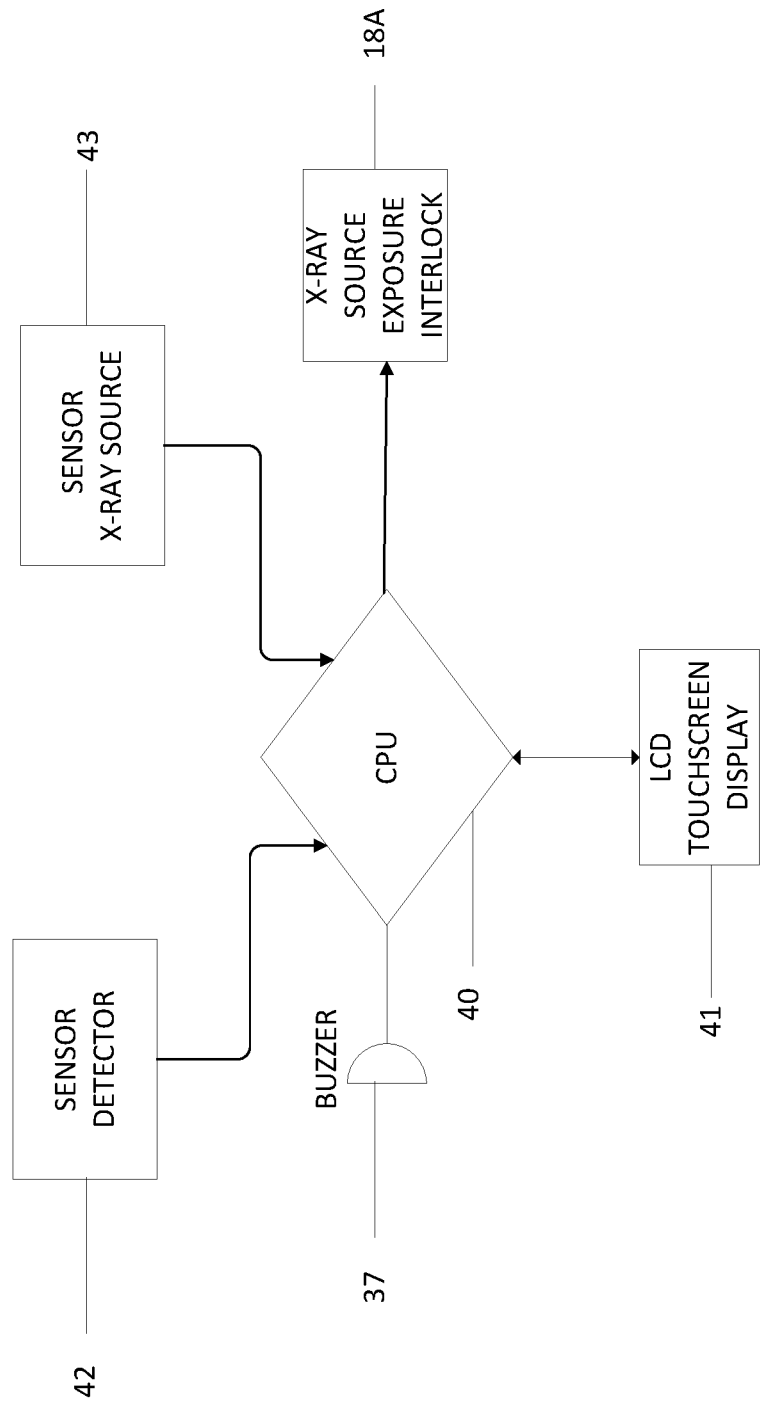
FIG. 6 is a schematic diagram of the computer and certain sensor inputs and outputs present in the device of FIG. 1.

As further illustrated in FIG. 6, alignment sensor/transmitters 42, 43 transmit data to the computer 40 from the signals produced by the alignment sensor/transmitters 42, 43. Those signals are processed by alignment system software located within computer 40 to ascertain the orientation distance and location of the detector 22 relative to the radiation source 18 to determine if the detector 22 is aligned normal to the path of stream of radiation 14 being emitted from the radiation source 18. The alignment system software within computer 40 sends process data to LCD display 41, and data received by LCD display 41 visually displays the location and orientation of detector 22 and the radiation source 18. When alignment in accordance with predetermined conditions is achieved, the computer 40 sends an activation signal to the radiation source 18, whereupon an audible indicator 37 and/or visual indicator 41 will activate to notify the operator that radiation 14 may be administered. The alignment sensor/transmitters 42, 43 may also be operable to indicate when the detector 22 is within range of the radiation source 18. Finally, the system 16 may be connected to the Internet or other communication network so that the images produced by the system 16 may be sent to a remote user, such as a radiologist's workstation. Importantly, the computer 40 may also be used to control the radiation source 18, such that emission of radiation 14 is prohibited until and unless the proper alignment conditions are achieved. Similarly, the computer 40 and the alignment software may be programmed to automatically permit emission of a radiation 14 dose for either radiographic or fluoroscopy images immediately upon achieving the predetermined alignment conditions. Thus, the present invention may be used to limit the patient's 11 exposure to unnecessary or excessive radiation 14 in a particular situation due to improper alignment. Until development of this system, such control over the emission of radiation by establishing this "interlock" 18A between alignment conditions and the radiation source has not been available in portable radiology imaging systems, fluoroscopy systems and particularly in the context of intensive care unit and neonatal intensive care unit applications.

Figure 3:
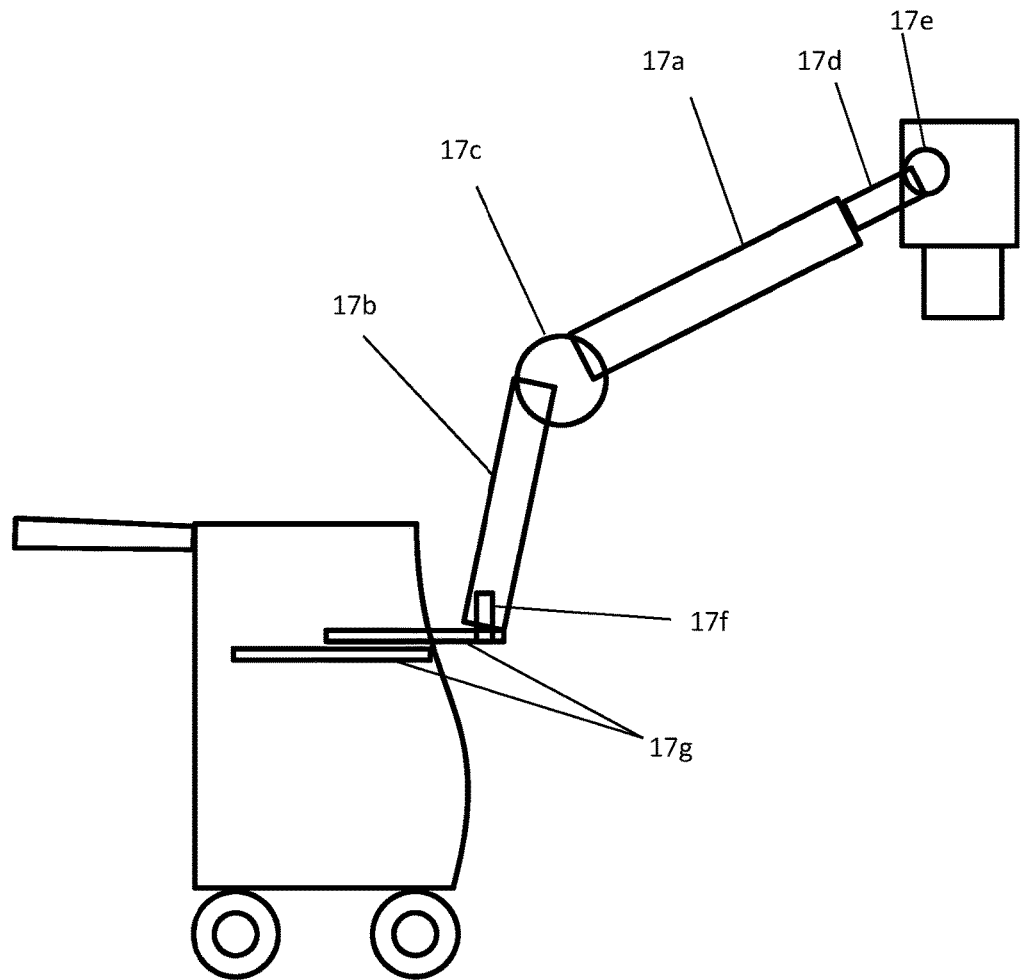
FIG. 3 illustrates more particularly in a side view features of the articulating support arm of the device of FIG. 1.

FIG. 3 illustrates the articulating tube support arm consist of vertical travel arm 17*a*, fix vertical support arm 17*b*, tube support arm pivot assembly 17*c*, tube support arm rotation assembly 17*f*, tube support arm longitudinal bearing assembly 17*g*, & 17*h*. Vertical travel arm 17*a* provides support and vertical movement of X-Ray tube assembly 18 (via, e.g., gas springs for biasing) to produce a counterbalancing force so x-ray tube assembly 18 and x-ray collimator 19 will remain in the vertical position they are place throughout the movement range allowed by pivot assembly 17*c*. Fix vertical arm 17*b* support the pivot assembly 17*c* for vertical travel arm 17*a*. Rotation shaft 17*e* provides transversal movement of X-Ray tube assembly 18. Longitudinal bearing track assembly 17*g* provides longitudinal movement for the x-ray tube assembly 18. Yoke 17*d* provides x-ray tube assembly 18 to rotate around the axis of vertical travel arm 17*a*. Tube rotation assembly 17*e* provides x-ray tube assemble to rotate longitudinal about is axis.

Figure 4:
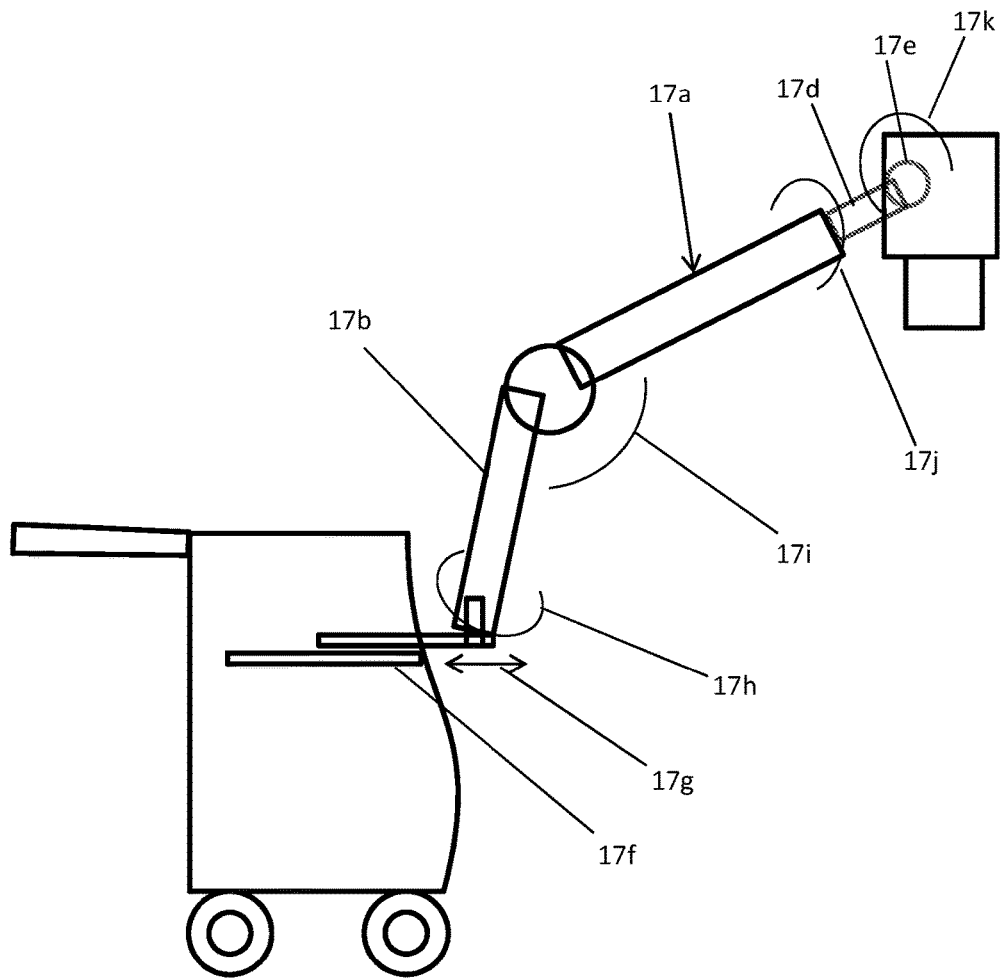
FIG. 4 illustrates range of movement of the articulating arm of the device of FIG. 1, to provide for x-ray source positioning.

FIG. 4 shows range of movement the articulating arm provides for x-ray source positioning in the device of FIG. 1. Thus, directions of rotational movement 17*g*, 17*h*, 17*i*, 17*j* and 17*k* illustrate the rotational motions of which the device is made capable for positioning the radiation source in a mobile radiologic or fluoroscopic application.

FIG. 5*a* illustrates the portable x-ray source of the device FIG. 1, comprising X-Ray tube head 18, X-Ray beam collimator 19, LCD monitor 41, collimator light 19B, laser positioning cross hair 19A, and lead aperture 19C. Positioning sensor 43 is housed or fix mounted within the X-Ray beam collimator enclosure 19.

FIG. 5*b* illustrates the portable detector 22 of the device, comprising the active imaging panel 22A, power supply 22B, and positioning sensor 42. All components are housed within the detector enclosure 22. It will be appreciated that the position detector sensor 42 and radiation source sensor 43 may be comprised of various sensors or electronic devices, including for example RFID tags, internal measurement units (IMUs), mobile tracking devices (MTDs), micro-electromechanical systems (MEMS), or the like, including combinations of two or more of the foregoing. Particular configurations will be determined by the design criteria and economics of a given system.

FIG. 6 is a schematic diagram of the FIG. 1 positioning system's sensors and computer controls, comprising detector sensor 42; radiation source sensor 43, alignment system computer/cpu 40, an alarm in the form of audible buzzer 37, radiation source exposure interlock 18A, and a user interface in the form of LCD monitor 41. As previously noted, radiation source and detector position information is fed from sensors 43 and 42, respectively, to computer 40, which in turn controls buzzer 37, interlock 18A and the output to user interface such as LCD monitor 41. A wide variety of control system software known to those of skill in the art can be adapted for execution on computer 40 to receive the signals from sensors 42 and 43 and control the operation of an alarm such as buzzer 37, interlock 18A and a user interface such as LCD monitor 41.

Figure 7B:
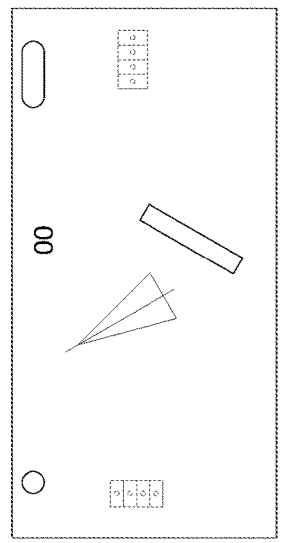
FIG. 7A-7D depict example representations of different views of the LCD monitor display in the embodiment of FIG. 1.
Figure 7D:
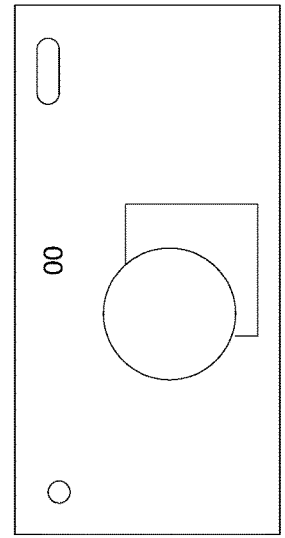
Figure 7A:
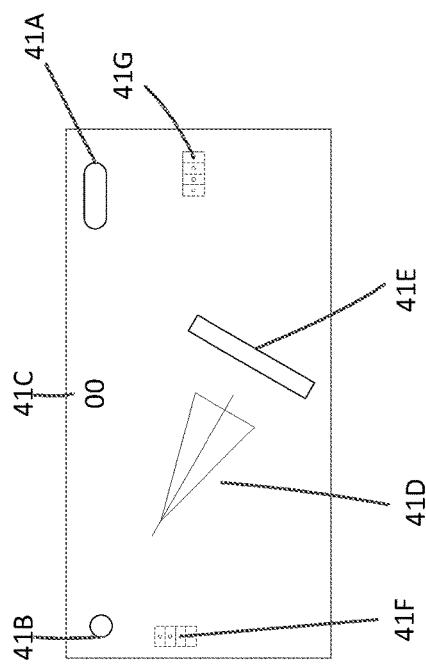
Figure 7C:
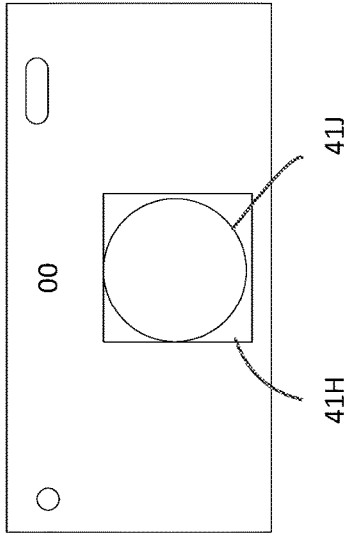

FIG. 7A-7D illustrate four (4) alternative examples of the LCD monitor 41 display of information to assist the operator with alignment of X-Ray source 18 to the portable detector 22. These screenshots illustrate examples of the type of information that may be available to the operator for positioning of radiation source 18 to the portable detector 22, or portable detector 22 to the radiation source 18. Various icons, LEDs, bar graph, or graphic symbols can be used to display position or orientation of radiation source 18 and detector 22 on LCD monitor 41. FIG. 7A shows LCD monitor positioning data if detector is placed at an oblique angle 41A "Start Icon" initiates sensors calibration and calculation of present position of detector 22 and radiation source 18. 41C displays distance between detector and radiation source, 41D is radiation source icon, 41E is detector icon, 41F is LED bar graph to show longitudinal position, 41G is LED bar graph to show transverse position, FIG. 7C shows LCD monitor positioning data if detector is place perpendicular: 41H is the detector, 41J is the radiation source FIGS. 7B & 7D shows LCD monitor positioning data when detector and radiation source are not aligned.

Figure 8:
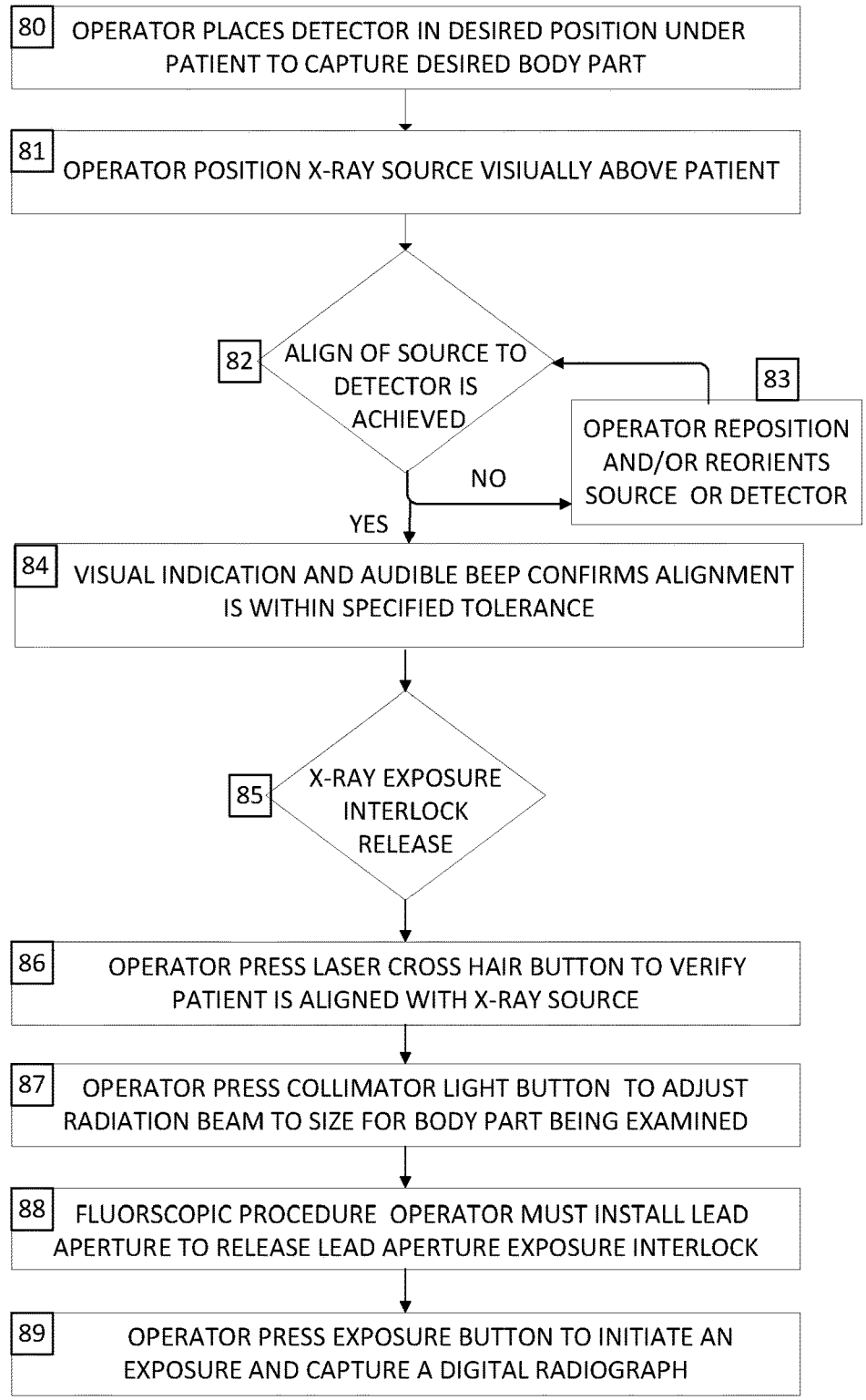
FIG. 8 is a work flow diagram for a typical X-ray examination employing the device of FIG. 1.

In FIG. 8 the work flow for a typical X-Ray exanimation employing a device of this invention is illustrated. In step 80, the operator first places the portable detector 22 under the patient (note: the portable detector 22 is usually no longer visible to the operator after placement). The portable detector 22 is positioned to ensure the body part to be examined is within the active imaging area 22A of the portable detector. In the next step 81, the operator then positions the portable radiation source 18 with the aid of data provide on LCD 41. Computer 40 may be automatically carrying out, or activated to carry out, calculations of radiation source 18 and portable detector 22 alignment via sensors/transmitters 43 and 42 installed on radiation source 18 and detector 22, respectively. System will prompt operator when calibration and positioning calculation are complete. Then in step 83, the system will accurately display location of portable detector 22 with respect to radiation source 18, and provide data of direction, angle, orientation, and/or distance operator has to move radiation source and/or portable detector to position radiation source to detector within predetermine tolerance(s). Upon successful alignment of radiation source to detector, at step 84 the system will active a visual 41B and/or audible signal 44 confirming alignment is within the predetermine tolerance(s). At step 85, the system will then release "Radiation interlock" 18A, and in step 86 operator will press laser cross hair button 19*b* to verify patient is align with radiation source 18. If patient is not aligned operator moves patient for proper alignment, and in step 87 operator presses the collimator light button to active collimator light source which displays a representation of the size of stream of radiation 14, and the operator adjusts the light size for size for body part being examined. In step 88, in addition, if operator has selected to perform a fluoroscopic procedure operator must installed lead aperture 19*c* to release lead aperture exposure interlock 19*cc*. When all conditions are met in step 89 operator can now initiate an X-ray exposure and capture the digital radiograph.

All references cited in this specification are herein incorporated by reference as though each reference was specifically and individually indicated to be incorporated by reference. The citation of any reference is for its disclosure prior to the filing date and should not be construed as an admission that the present invention is not entitled to ante-date such reference by virtue of prior invention.

It will be understood that each of the elements described above, or two or more together may also find a useful application in other types of methods differing from the type described above. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention set forth in the appended claims. The foregoing embodiments are presented by way of example only; the scope of the present invention is to be limited only by the following claims.

What is claimed is:

1. An alignment control system, comprising:
   an alignment computer comprising a central processing unit and software, the software when executed by the central processing unit cause the central processing unit to:
   receive a first set of alignment data from a plurality of sensors associated to a radiation source;
   receive a second set of alignment data from a plurality of sensors associated to a portable detector;

if an alignment condition between the first set of alignment data and the second set of alignment data has achieved one or more predetermined alignment conditions, send an activation signal to the radiation source to indicate that radiation may be emitted;

continuously monitor alignment conditions to prevent emission of radiation, by the radiation source, if the first set of alignment data and the second set of alignment data have not achieved the one or more alignment conditions.

2. The system of claim 1, wherein the first set of alignment data comprises, at least a first position, a first distance and a first orientation of the radiation source and the second set of alignment data comprises, at least a second position, a second distance and a second orientation of the portable detector.

3. The system of claim 2, wherein the predetermined alignment conditions are within two percent of the first distance and the second distance.

4. The system of claim 1, wherein the alignment computer enables automatic emission of radiation, by the radiation source, upon and during achievement of the one or more predetermined alignment conditions.

5. The system of claim 1, wherein the alignment computer further comprises an indicator operable to notify an operator when the first set of alignment data and the second set of alignment data have achieved the one or more predetermined alignment conditions.

6. The system of claim 5, wherein the indicator is operable to notify an operator when the first set of alignment data is within a predetermined range of the second set of alignment data.

7. An alignment control method, comprising the steps of:
receiving, at an alignment computer, a first set of alignment data from a plurality of sensors associated to a radiation source;

receiving, at the alignment computer, a second set of alignment data from a plurality of sensors associated to a portable detector;

if an alignment condition between the first set of alignment data and the second set of alignment data is achieved one or more predetermined alignment conditions, sending, by the alignment computer, an activation signal to the radiation source to indicate that radiation may be emitted;

continuously monitoring, by the alignment computer, alignment conditions to prevent emission of radiation, by the radiation source, if the first set of alignment data and the second set of alignment data have not achieved the one or more alignment conditions.

8. The method of claim 7, wherein the first set of alignment data comprises, at least, a first position, a first distance and a first orientation of the radiation source and the second set of alignment data comprises, at least, a second position, a second distance and a second orientation of the portable detector.

9. The method of claim 8, wherein the predetermined alignment conditions are within two percent of the first distance and the second distance.

10. The method of claim 7, further comprising the step of enabling, by the alignment computer, automatic emission of radiation, by the radiation source, upon and during achievement of the one or more predetermined alignment conditions.

11. The method of claim 7, wherein the alignment computer comprises an indicator operable to notify an operator when the first set of alignment data and the second set of alignment data have achieved the one or more predetermined alignment conditions.

12. The method of claim 11, wherein the indicator is operable to notify an operator when the first set of alignment data is within a predetermined range of the second set of alignment data.

* * * * *